US010098716B2

(12) United States Patent
Ritzberger et al.

(10) Patent No.: US 10,098,716 B2
(45) Date of Patent: Oct. 16, 2018

(54) LITHIUM SILICATE GLASS CERAMIC AND GLASS WITH HEXAVALENT METAL OXIDE

(71) Applicant: Ivoclar Vivadent AG, Schaan (LI)

(72) Inventors: Christian Ritzberger, Grabs (CH); Elke Apel, Oberschan (CH); Wolfram Höland, Schaan (LI); Volker Rheinberger, Vaduz (LI)

(73) Assignee: Ivoclar Vivadent AG, Schaan (LI)

( * ) Notice: Subject to any disclaimer, the term of this patent is extended or adjusted under 35 U.S.C. 154(b) by 0 days.

(21) Appl. No.: 15/195,125

(22) Filed: Jun. 28, 2016

(65) Prior Publication Data

US 2016/0302898 A1 Oct. 20, 2016

Related U.S. Application Data

(63) Continuation of application No. 14/001,190, filed as application No. PCT/EP2012/070224 on Oct. 11, 2012, now Pat. No. 9,403,714.

(30) Foreign Application Priority Data

Oct. 14, 2011 (EP) .................................... 11185340

(51) Int. Cl.
C03C 10/00 (2006.01)
A61C 13/083 (2006.01)
C03C 3/083 (2006.01)
C03C 3/097 (2006.01)
C03C 4/00 (2006.01)
A61C 13/00 (2006.01)
A61C 13/09 (2006.01)
C03C 23/00 (2006.01)

(52) U.S. Cl.
CPC ........ A61C 13/083 (2013.01); A61C 13/0006 (2013.01); A61C 13/09 (2013.01); C03C 3/083 (2013.01); C03C 3/097 (2013.01); C03C 4/0021 (2013.01); C03C 10/00 (2013.01); C03C 10/0027 (2013.01); C03C 23/007 (2013.01); C03C 2204/00 (2013.01)

(58) Field of Classification Search
CPC .. C03C 10/0009; C03C 10/0027; C03C 10/00
USPC .......................................................... 501/5
See application file for complete search history.

(56) References Cited

U.S. PATENT DOCUMENTS

| 2,684,911 A | 7/1954 | Stookey |
| 3,006,775 A | 10/1961 | Chen |
| 3,022,180 A | 2/1962 | Morrissey et al. |
| 3,161,528 A | 12/1964 | Eppler |
| 3,252,778 A | 5/1966 | Goodman et al. |
| 3,379,542 A | 4/1968 | McMillan et al. |
| 3,804,608 A | 4/1974 | Gaskell et al. |
| 3,816,704 A | 6/1974 | Borom et al. |
| 3,977,857 A * | 8/1976 | Mattox .................. C03B 19/02 156/242 |
| 4,155,888 A | 5/1979 | Mooth |
| 4,189,325 A | 2/1980 | Barrett et al. |
| 4,414,282 A | 11/1983 | McCollister et al. |
| 4,473,653 A | 9/1984 | Rudoi |
| 4,480,044 A | 10/1984 | McAlinn |
| 4,515,634 A | 5/1985 | Wu et al. |
| 4,671,770 A | 6/1987 | Bell et al. |
| 4,963,707 A | 10/1990 | Zyokou et al. |
| 4,977,114 A | 12/1990 | Horinouchi et al. |
| 5,176,961 A | 1/1993 | Crooker et al. |
| 5,219,799 A * | 6/1993 | Beall .................. C03C 10/0009 501/5 |
| 5,432,130 A | 7/1995 | Rheinberger et al. |
| 5,507,981 A | 4/1996 | Petticrew et al. |
| 5,580,363 A * | 12/1996 | Goto ........................ C03C 4/02 356/237.2 |
| 5,618,763 A | 4/1997 | Frank et al. |
| 5,628,564 A | 5/1997 | Nenyei et al. |
| 5,691,256 A | 11/1997 | Taguchi et al. |
| 5,698,019 A | 12/1997 | Frank et al. |
| 5,698,482 A | 12/1997 | Frank et al. |
| 5,702,514 A | 12/1997 | Petticrew |
| 5,707,777 A | 1/1998 | Aoai et al. |
| 5,872,069 A | 2/1999 | Abe |
| 5,874,376 A | 2/1999 | Taguchi et al. |
| 5,925,180 A | 7/1999 | Frank et al. |
| 5,938,959 A | 8/1999 | Wang |
| 5,968,856 A | 10/1999 | Schweiger et al. |
| 6,066,584 A | 5/2000 | Krell et al. |
| 6,095,682 A | 8/2000 | Hollander et al. |

(Continued)

FOREIGN PATENT DOCUMENTS

BY   11288 C1    10/2008
CA   2163792 A1  12/1994

(Continued)

OTHER PUBLICATIONS

Durschang, DR. Bernhard, "Report of Results", Fraunhofer Institute for Silicate Research ISC Glass and Mineral Materials, 2015.
McMillan, P.W., et al., "The Structure and Properties of a Lithium Zinc Silicate Glass-Ceramic", Journal of Material Science 1966, I. 269-279.
Deubener, J., et al., "Induction time analysis of nucleation and crystal grown in di- and metasilicate glasses", Journal of Non-Crystalline Solids 1993, 163, 1-12.
Holand, W., et al., "Glass-ceramic technology", American Chemical Society 2002, Westerville OH, USA.
Holand, W., et al., "Control of nucleation in glass ceramics", Phil. Trans. Soc. Lond. A 2003, 361, 575-589.
Holand, W., et al., "Principles and phenomena of bioengineering with glass-ceramics of dental restoration", Journal of the European Ceramics Society 2007, 27, 1571-1577.

(Continued)

Primary Examiner — Noah S Wiese
(74) Attorney, Agent, or Firm — Ann M. Knab; Thad McMurray

(57) ABSTRACT

Lithium silicate glass ceramics and glasses containing specific oxides of hexavalent elements are described which crystallize at low temperatures and are suitable in particular as dental materials.

21 Claims, No Drawings

(56) References Cited

U.S. PATENT DOCUMENTS

| | | |
|---|---|---|
| 6,106,747 A | 8/2000 | Wohlwend |
| 6,121,175 A | 9/2000 | Drescher et al. |
| 6,048,589 A | 11/2000 | Suzuki |
| 6,157,004 A | 12/2000 | Bizzio |
| 6,163,020 A | 12/2000 | Bartusch et al. |
| 6,174,827 B1 | 1/2001 | Goto et al. |
| 6,252,202 B1 | 6/2001 | Zychek |
| 6,267,595 B1 | 7/2001 | Gratz |
| 6,270,876 B1 * | 8/2001 | Abe .................... C03C 10/0027 428/141 |
| 6,287,121 B1 | 9/2001 | Guiot et al. |
| 6,342,458 B1 | 1/2002 | Schweiger et al. |
| 6,372,319 B1 * | 4/2002 | Abe .................... C03C 10/0027 428/141 |
| 6,376,397 B1 | 4/2002 | Petticrew |
| 6,420,288 B2 | 7/2002 | Schweiger et al. |
| 6,426,311 B1 | 7/2002 | Goto et al. |
| 6,441,346 B1 | 8/2002 | Zychek |
| 6,455,451 B1 * | 9/2002 | Brodkin ................ A61K 6/033 106/35 |
| 6,485,849 B2 | 11/2002 | Petticrew |
| 6,514,893 B1 | 2/2003 | Schweiger et al. |
| 6,517,623 B1 | 2/2003 | Brodkin et al. |
| 6,582,826 B1 | 6/2003 | Goto et al. |
| 6,593,257 B1 | 7/2003 | Nagata et al. |
| 6,794,043 B2 * | 9/2004 | Goto .................... C03C 10/0027 428/426 |
| 6,802,894 B2 | 10/2004 | Brodkin et al. |
| 6,818,573 B2 | 11/2004 | Petticrew |
| 7,162,321 B2 | 1/2007 | Luthardt et al. |
| 7,316,740 B2 | 1/2008 | Rheinberger et al. |
| 7,452,836 B2 | 11/2008 | Apel et al. |
| 7,655,586 B1 | 2/2010 | Brodkin et al. |
| 7,806,694 B2 | 10/2010 | Brodkin et al. |
| 7,816,291 B2 | 10/2010 | Schweiger et al. |
| 7,867,930 B2 | 1/2011 | Apel et al. |
| 7,867,933 B2 | 1/2011 | Apel et al. |
| 7,871,948 B2 | 1/2011 | Apel et al. |
| 7,892,995 B2 | 2/2011 | Castillo |
| 7,993,137 B2 | 8/2011 | Apel et al. |
| 8,042,358 B2 | 10/2011 | Schweiger et al. |
| 8,047,021 B2 | 11/2011 | Schweiger et al. |
| 8,444,756 B2 | 5/2013 | Schweiger et al. |
| 2001/0006174 A1 | 7/2001 | Brennan |
| 2001/0031446 A1 | 10/2001 | Petticrew |
| 2002/0010063 A1 | 1/2002 | Schweiger et al. |
| 2002/0022563 A1 | 2/2002 | Schweiger et al. |
| 2002/0031670 A1 | 3/2002 | Goto |
| 2002/0160694 A1 | 10/2002 | Wood et al. |
| 2003/0012961 A1 | 1/2003 | Goto et al. |
| 2003/0073563 A1 | 4/2003 | Brodkin et al. |
| 2004/0182538 A1 | 9/2004 | Lambrecht |
| 2005/0098064 A1 | 5/2005 | Schweiger et al. |
| 2005/0127544 A1 | 6/2005 | Brodkin et al. |
| 2006/0035025 A1 | 2/2006 | Verplancken et al. |
| 2006/0082033 A1 | 4/2006 | Hauptmann et al. |
| 2006/0139091 A1 | 6/2006 | Fratti |
| 2006/0257823 A1 | 11/2006 | Pfeiffer et al. |
| 2006/0257824 A1 | 11/2006 | Pfeiffer et al. |
| 2007/0023971 A1 | 2/2007 | Saha et al. |
| 2007/0042889 A1 | 2/2007 | Apel et al. |
| 2008/0120994 A1 | 5/2008 | Schweiger et al. |
| 2008/0199823 A1 | 8/2008 | Miller |
| 2009/0023574 A1 | 1/2009 | Holand et al. |
| 2009/0038344 A1 | 2/2009 | Apel et al. |
| 2009/0038508 A1 | 2/2009 | Apel et al. |
| 2009/0042166 A1 | 2/2009 | Craig et al. |
| 2009/0256274 A1 | 10/2009 | Castillo |
| 2009/0258778 A1 | 10/2009 | Castillo |
| 2010/0083706 A1 | 4/2010 | Castillo |
| 2011/0030423 A1 | 2/2011 | Johannes et al. |
| 2011/0256409 A1 * | 10/2011 | Ritzberger ............ A61K 6/0215 428/432 |
| 2012/0094822 A1 | 4/2012 | Castillo et al. |
| 2012/0148988 A1 | 6/2012 | Castillo et al. |
| 2012/0309607 A1 | 12/2012 | Durschang et al. |
| 2014/0141960 A1 | 5/2014 | Borczuch-Laczka et al. |

FOREIGN PATENT DOCUMENTS

| | | |
|---|---|---|
| CA | 2213390 | 3/1998 |
| CA | 2239865 | 12/1998 |
| CA | 2239869 | 12/1998 |
| CA | 2252660 | 5/1999 |
| CA | 2252660 A1 | 5/1999 |
| CA | 2351154 | 12/2001 |
| DE | 2451121 | 5/1975 |
| DE | 4303458 C1 | 1/1994 |
| DE | 4314817 | 11/1994 |
| DE | 4423793 | 2/1996 |
| DE | 4423794 | 2/1996 |
| DE | 4428839 | 2/1996 |
| DE | 19647739 | 3/1998 |
| DE | 19725553 | 12/1998 |
| DE | 19725555 | 12/1998 |
| DE | 10031431 | 1/2002 |
| DE | 102007011337 | 9/2008 |
| EP | 231773 | 8/1987 |
| EP | 0827941 | 3/1998 |
| EP | 0916625 | 5/1999 |
| EP | 1152641 A2 | 11/2001 |
| EP | 1505041 | 2/2005 |
| EP | 1688398 | 8/2006 |
| EP | 2377830 | 10/2011 |
| GB | 752243 A | 7/1956 |
| GB | 1063291 A | 3/1967 |
| GB | 2284655 A | 6/1995 |
| JP | S4011945 B1 | 6/1965 |
| JP | H10323354 A | 12/1998 |
| JP | 11-74418 A | 3/1999 |
| JP | 2005-062832 A | 3/2005 |
| RU | 2101238 C1 | 1/1998 |
| WO | 2007028787 A1 | 3/2007 |
| WO | 2008106958 | 9/2008 |
| WO | 2009126317 | 10/2009 |
| WO | 2011076422 | 6/2011 |

OTHER PUBLICATIONS

Apel, E., et al., "Influence of ZrO2 on the crystallization and properties of lithium disilicate glass-ceramics derived from multi-component system," Journal of the European Ceramic Society, 2007, 27, 1571-1577.

Ivoclar Vivadent, Inc., IPS e.max lithium disilicate, 627329, Rev. Feb. 2009.

Borom, M.P., et al., "Strength and Microstructure in Lithium Disilicate Glass Ceramics", J. Am. Ceram. Soc., 1975,58, 385-391.

Stookey, S.D., "Chemical Machining of Photosensitive Glass," Ind. Eng. Chem. 45:115-118 (1993).

Von Clausbruch, et al., "Effect of ZnO on the Crystallization, Microstructure, and Properties of Glass-Ceramics in the SiO2—Li2O—K2O—P2O5 System," Glastech. Ber. Glass Sci. Technol. 74(8):223-229(2001).

Von Clausbruch, et al., "Effect of P2O5 on the Crystallization and Microstructure of Glass-Ceramics in the SiO2—Li2O—Zn)—P2O5 System," Glastech. Ber. Glass Sci. Technol. 74(8):223-229(2001).

Oliveria et al., "Sintering and Crystallization of a GlassPowder in the Li2O—ZrO2—SiO2 System," J. Amer. Ceramic Soc. 81(3):777-780 (1998).

Giassi, et al., "Injection Moulding of LiO2—ZrO2—SiO2—Al2O3 (LZSA) Glass Ceramics," Glass Technol., 46(3), 277-280 (2005).

http://enwikipedia.org/wiki/Nucleation; Sep. 20, 2012.

McMillan, P.W., "Glass Ceramics," Moscow, Mir 1967.

Jakovac, M., et al., Measurement of ion elution from dental ceramics, Journal of the European Ceramic Society, May 6, 2006, vol. 26, pp. 1695-1700.

Montedo, et al., "Low Thermal Expansion Sintered LZSA Glass Ceramics," American Ceramic Society Bulletin, vol. 87, No. 7, 99. 34-40. Jul. 2008.

(56) References Cited

OTHER PUBLICATIONS

"Arsenic and Arsenic Compounds," IARC Monograph, vol. 100C pp. 41-93, 2012.
"Antimony Trioxide and Antimony Trisulfide", IARC Monograph, vol. 47, pp. 291-305, 1989.

* cited by examiner

LITHIUM SILICATE GLASS CERAMIC AND GLASS WITH HEXAVALENT METAL OXIDE

CROSS-REFERENCE TO RELATED APPLICATIONS

This application is a continuation application of U.S. application Ser. No. 14/001,190, filed Aug. 23, 2013, which is the National Stage filing of International patent application PCT/EP2012/070224, filed on Oct. 11, 2012, which claims priority to European patent application No. 11185340.4 filed on Oct. 14, 2011, the disclosures of which are incorporated herein by reference in their entirety.

TECHNICAL FIELD

The invention relates to lithium silicate glass ceramic and glass which contain hexavalent metal oxide selected from $MoO_3$, $WO_3$ and mixtures thereof and are particularly suitable for use in dentistry, preferably for the preparation of dental restorations.

BACKGROUND OF THE INVENTION

Lithium silicate glass ceramics are characterized as a rule by very good mechanical properties, which is why they have been used for a long time in the dental field and there primarily for the preparation of dental crowns and small bridges. The known lithium silicate glass ceramics usually contain as main components $SiO_2$, $Li_2O$, $Na_2O$ or $K_2O$, and nucleating agents such as $P_2O_5$ as well as additional components.

DE 24 51 121 describes lithium disilicate glass ceramics which contain $K_2O$ and $Al_2O_3$. They are prepared from corresponding nuclei-containing starting glasses which are heated to temperatures of from 850 to 870° C. for the crystallization of lithium disilicate. The purpose for which the glass ceramics are used is not disclosed.

EP 827 941 describes sinterable lithium disilicate glass ceramics for dental purposes, which also contain $K_2O$ or $Na_2O$ in addition to $La_2O_3$. The lithium disilicate crystal phase is produced at a temperature of 850° C.

Lithium disilicate glass ceramics which likewise contain $La_2O_3$ as well as $K_2O$ are known from EP 916 625. A heat treatment is carried out at 870° C. for the formation of lithium disilicate.

EP 1 505 041 describes lithium silicate glass ceramics containing $K_2O$, which, when lithium metasilicate is present as main crystal phase, can be very satisfactorily machined e.g. by means of CAD/CAM processes, in order to then be converted by further heat treatment at temperatures of from 830 to 850° C. into high-strength lithium disilicate glass ceramics.

EP 1 688 398 describes similar $K_2O$-containing lithium silicate glass ceramics which are moreover substantially free from ZnO. A heat treatment at 830 to 880° C. is applied to them to produce lithium disilicate.

U.S. Pat. No. 5,507,981 describes processes for producing dental restorations and glass ceramics that can be used in these processes. These are in particular lithium disilicate glass ceramics with a low level of $Li_2O$ which contain as a rule either $Na_2O$ or $K_2O$.

U.S. Pat. No. 6,455,451 relates to lithium disilicate glass ceramics which contain further alkali metal oxides in addition to $Li_2O$. However, the production of the desired lithium disilicate crystal phase requires high temperatures of from 800 to 1000° C.

WO 2008/106958 discloses lithium disilicate glass ceramics for veneering zirconium oxide ceramics. The glass ceramics contain $Na_2O$ and are produced by heat treatment of nuclei-containing glasses at 800 to 940° C.

WO 2009/126317 describes $GeO_2$-containing lithium metasilicate glass ceramics which also contain $K_2O$. The glass ceramics are processed to form dental products primarily by machining.

WO 2011/076422 relates to lithium disilicate glass ceramics which also contain $K_2O$ in addition to high levels of $ZrO_2$ or $HfO_2$. The crystallization of lithium disilicate takes place at high temperatures of from 800 to 1040° C.

Common to the known lithium disilicate glass ceramics is that they require heat treatments at more than 800° C. in order to effect the precipitation of lithium disilicate as main crystal phase. A large quantity of energy is therefore also necessary for their preparation. Further, with the known glass ceramics the alkali metal oxides, such as in particular $K_2O$ or $Na_2O$, are as a rule present as essential components which are apparently required for the production of glass ceramics with the desired properties and in particular the formation of the sought lithium disilicate main crystal phase.

SUMMARY OF THE INVENTION

There is therefore a need for lithium silicate glass ceramics during the preparation of which the crystallization of lithium disilicate can be effected at lower temperatures. Further, they should also be able to be prepared without the alkali metal oxides, such as $K_2O$ or $Na_2O$, previously regarded as necessary, and be suitable in particular for the preparation of dental restorations primarily on the basis of their optical and mechanical properties.

This object is achieved by the lithium silicate glass ceramic according to the attached claims. Also a subject of the invention are the starting glass, the lithium silicate glass with nuclei, the process for the preparation of the glass ceramic and the lithium silicate glass with nuclei according to the attached claims.

DETAILED DESCRIPTION OF THE INVENTION

The lithium silicate glass ceramic according to the invention is characterized in that it comprises hexavalent metal oxide selected from $MoO_3$, $WO_3$ and mixtures thereof.

It is preferred that the glass ceramic comprises the hexavalent metal oxide or mixtures thereof in an amount of from 0.1 to 8.4, in particular 0.1 to 8.0, particularly preferred 1.5 to 8.0 and even more preferred 2.0 to 5.0 wt.-%.

It is particularly surprising that the formation of the glass ceramic according to the invention with lithium disilicate as main crystal phase is also achieved in the absence of various components regarded as necessary for conventional glass ceramics and in particular alkali metal oxides such as $K_2O$, even at very low and thus advantageous crystallization temperatures of in particular from 520 to 750° C. The glass ceramic also has a combination of optical and mechanical properties as well as processing properties that are very advantageous for the use as dental materials.

The glass ceramic according to the invention accordingly preferably comprises less than 2.0, in particular less than 0.5 wt.-%, preferably less than 0.1 wt.-% $K_2O$. It is particularly preferably substantially free from $K_2O$.

In a further preferred embodiment, the glass ceramic comprises less than 1.0, in particular less than 0.5 and preferably less than 0.1 wt.-% further alkali metal oxide and particularly preferred is substantially free therefrom. The term "further alkali metal oxide" refers to alkali metal oxide with the exception of $Li_2O$.

A glass ceramic, excluding lithium silicate glass ceramic which comprises at least 6.1 wt.-% $ZrO_2$, is also preferred.

Further, a glass ceramic, excluding lithium silicate glass ceramic which comprises at least 8.5 wt.-% transition metal oxide selected from the group consisting of oxides of yttrium, oxides of transition metals with an atomic number from 41 to 79 and mixtures of these oxides, is also preferred.

The glass ceramic according to the invention preferably comprises 60.0 to 85.0, in particular 65.0 to 80.0 and preferably 69.0 to 77.0 wt.-% $SiO_2$.

It is also preferred that the glass ceramic comprises 12.0 to 20.0 and in particular 15.0 to 17.0 wt.-% $Li_2O$.

It is further preferred that the molar ratio between $SiO_2$ and $Li_2O$ is from 1.7 to 3.1, in particular 1.8 to 3.0. It is very surprising that the production of lithium disilicate is achieved within this broad range. Specifically at ratios of less than 2.0 customary materials usually form lithium metasilicate instead of lithium disilicate.

In a further preferred embodiment the molar ratio between $SiO_2$ and $Li_2O$ is at least 2.2, in particular 2.3 to 2.5, and preferably about 2.4, as a glass ceramic with particularly high strength is thus obtained.

The glass ceramic according to the invention can also comprise a nucleating agent. $P_2O_5$ is particularly preferably used for this. The glass ceramic preferably comprises 0 to 10.0, in particular 2.0 to 9.0, and preferably 3.0 to 7.5 wt.-% $P_2O_5$.

In a further preferred embodiment, the glass ceramic comprises at least one and preferably all of the following components:

| Component | wt.-% |
| --- | --- |
| $SiO_2$ | 69.0 to 77.0 |
| $Li_2O$ | 12.0 to 20.0 |
| hexavalent metal oxide or mixtures | 2.0 to 5.0 |
| $P_2O_5$ | 0 to 7.0, in particular 3.0 to 7.0 |
| $Al_2O_3$ | 0 to 6.0, in particular 3.0 to 5.0. |

The glass ceramic according to the invention can moreover also comprise additional components which are selected in particular from oxides of trivalent elements and further oxides of tetravalent elements, melt accelerators, colourants and fluorescent agents. It is, however, preferred that the glass ceramic is free from arsenic oxide and antimony oxide. These oxides are used in glass ceramics for technical applications as agents for homogenizing the melt. As they are potentially damaging to health, they are to be avoided in the glass ceramic according to the invention as this is used in particular as dental material.

Suitable oxides of trivalent elements are in particular $Al_2O_3$, $Y_2O_3$ and $Bi_2O_3$ and mixtures thereof, and preferably $Al_2O_3$, already mentioned above as a component. These oxides are used in particular in an amount of from 0 to 4.0 wt.-%.

The term "further oxides of tetravalent elements" refers to oxides of tetravalent elements with the exception of $SiO_2$. Examples of suitable further oxides of tetravalent elements are $TiO_2$, $SnO_2$, $GeO_2$ and $ZrO_2$, in particular $ZrO_2$. These oxides are used in particular in an amount of from 0 to 4.0 wt.-%.

A glass ceramic which comprises at least one oxide of trivalent elements and/or at least one further oxide of tetravalent elements is preferred.

Examples of melt accelerators are fluorides.

Examples of colourants and fluorescent agents are oxides of d- and f-elements, such as the oxides of Ti, V, Sc, Mn, Fe, Co, Ta, W, Ce, Pr, Nd, Tb, Er, Dy, Gd, Eu and Yb. Metal colloids, e.g. of Ag, Au and Pd, can also be used as colourants and in addition can also act as nucleating agents. These metal colloids can be formed e.g. by reduction of corresponding oxides, chlorides or nitrates during the melting and crystallization processes. The metal colloids can be present in the glass ceramic in an amount of from 0.005 to 0.5 wt.-%.

The term "main crystal phase" used below refers to the crystal phase which has the highest proportion by volume compared with other crystal phases.

The glass ceramic according to the invention has lithium metasilicate as main crystal phase in one embodiment. In particular the glass ceramic comprises more than 5 vol.-%, preferably more than 10 vol.-% and particularly preferred more than 15 vol.-% lithium metasilicate crystals, relative to the total glass ceramic.

In a further particularly preferred embodiment, the glass ceramic has lithium disilicate as main crystal phase. In particular the glass ceramic comprises more than 10 vol.-%, preferably more than 20 vol.-% and particularly preferably more than 30 vol.-% lithium disilicate crystals, relative to the total glass ceramic.

The lithium disilicate glass ceramic according to the invention is characterized by particularly good mechanical properties and can be produced e.g. by heat treatment of the lithium metasilicate glass ceramic according to the invention. However, it can be formed in particular by heat treatment of a corresponding starting glass or of a corresponding lithium silicate glass with nuclei.

It has surprisingly been shown that the lithium disilicate glass ceramic according to the invention has very good mechanical and optical properties and processing properties even in the absence of components regarded as essential for conventional glass ceramics. The combination of its properties even allows it to be used as dental material and in particular material for the preparation of dental restorations.

The lithium disilicate glass ceramic according to the invention has in particular a fracture toughness, measured as $K_{IC}$ value, of at least 1.5 MPa·m$^{0.5}$ and in particular more than approximately 1.8 MPa·m$^{0.5}$. This value was determined using the Vickers method and calculated using Niihara's equation.

The invention also relates to a lithium silicate glass with nuclei that are suitable for forming lithium metasilicate and/or lithium disilicate crystals, wherein the glass comprises the components of the above-described glass ceramics according to the invention. Thus, this glass is characterized in that it comprises hexavalent metal oxide selected from $MoO_3$, $WO_3$ and mixtures thereof. In respect of preferred embodiments of this glass reference is made to the preferred embodiments described above of the glass ceramics according to the invention.

The glass with nuclei according to the invention can be produced by heat treatment of a correspondingly composed starting glass according to the invention. The lithium metasilicate glass ceramic according to the invention can then be formed by a further heat treatment, and in turn be converted into the lithium disilicate glass ceramic according to the invention by further heat treatment, or the lithium disilicate glass ceramic according to the invention can also preferably be formed directly from the glass with nuclei. The starting glass, the glass with nuclei and the lithium metasilicate glass ceramic can consequently be regarded as precursors for the production of the high-strength lithium disilicate glass ceramic.

The glass ceramics according to the invention and the glasses according to the invention are present in particular in the form of powders, granular material or blanks, e.g. monolithic blanks, such as platelets, cuboids or cylinders, or powder green compacts, in unsintered, partly sintered or densely-sintered form. They can easily be further processed in these forms. They can, however, also be present in the form of dental restorations for use in the oral cavity, such as inlays, onlays, crowns, veneers, facets or abutments.

The invention also relates to a process for the preparation of the glass ceramic according to the invention and the glass with nuclei according to the invention, wherein a correspondingly composed starting glass, the glass with nuclei according to the invention or the lithium metasilicate glass ceramic according to the invention is subjected to at least one heat treatment in the range of from 450 to 950° C., in particular 450 to 750 and preferably 480 to 750° C.

The starting glass according to the invention is therefore characterized in that it comprises hexavalent metal oxide selected from $MoO_3$, $WO_3$ and mixtures thereof. In addition, it preferably also comprises suitable amounts of $SiO_2$ and $Li_2O$, in order to allow the formation of a lithium silicate glass ceramic, and in particular a lithium disilicate glass ceramic.

Further, the starting glass can also comprise still further components, such as are given above for the lithium silicate glass ceramic according to the invention. All those embodiments are preferred for the starting glass which are also given as preferred for the glass ceramic.

With the process according to the invention, the glass with nuclei is usually prepared by means of a heat treatment of the starting glass at a temperature of in particular from 480 to 500° C. The lithium disilicate glass ceramic according to the invention is then preferably produced from the glass with nuclei through further heat treatment at usually 520 to 750° C.

Thus, much lower temperatures are used according to the invention for the crystallization of lithium disilicate than with the conventional lithium disilicate glass ceramics. The energy thus saved represents a clear advantage. Surprisingly, this low crystallization temperature is also possible in the absence of components, such as further alkali metal oxides, regarded as essential for conventional glass ceramics.

To prepare the starting glass, the procedure is in particular that a mixture of suitable starting materials, such as carbonates, oxides, phosphates and fluorides, is melted at temperatures of in particular from 1300 to 1600° C. for 2 to 10 h. To achieve a particularly high homogeneity, the obtained glass melt is poured into water in order to form a granular glass material, and the obtained granular material is then melted again.

The melt can then be poured into moulds to produce blanks of the starting glass, so-called solid glass blanks or monolithic blanks.

It is also possible to put the melt into water again in order to prepare a granular material. This granular material can then be pressed, after grinding and optionally addition of further components, such as colourants and fluorescent agents, to form a blank, a so-called powder green compact.

Finally, the starting glass can also be processed to form a powder after granulation.

The starting glass, e.g. in the form of a solid glass blank, a powder green compact or in the form of a powder, is then subjected to at least one heat treatment in the range of from 450 to 950° C. It is preferred that a first heat treatment is initially carried out at a temperature in the range of from 480 to 500° C. to prepare a glass according to the invention with nuclei which are suitable for forming lithium metasilicate and/or lithium disilicate crystals. This first heat treatment is preferably carried out for a period of from 10 min to 120 min and in particular 10 min to 30 min. The glass with nuclei can then preferably be subjected to at least one further temperature treatment at a higher temperature and in particular more than 570° C. to effect crystallization of lithium metasilicate or lithium disilicate. This further heat treatment is preferably carried out for a period of from 10 min to 120 min, in particular 10 min to 60 min and particularly preferred 10 to 30 min. To crystallize lithium disilicate, the further heat treatment is usually carried out at 520 to 750° C.

Therefore, in a preferred embodiment of the process
(a) the starting glass is subjected to a heat treatment at a temperature of from 480 to 500° C. in order to form the glass with nuclei, and
(b) the glass with nuclei is subjected to a heat treatment at a temperature of from 520 to 750° C. in order to form the glass ceramic with lithium disilicate as main crystal phase.

The duration of the heat treatments carried out in (a) and (b) is preferably as given above.

The at least one heat treatment carried out in the process according to the invention can also take place during a hot pressing or sintering-on of the glass according to the invention or the glass ceramic according to the invention.

Dental restorations, such as bridges, inlays, onlays, crowns, veneers, facets or abutments, can be prepared from the glass ceramics according to the invention and the glasses according to the invention. The invention therefore also relates to their use for the preparation of dental restorations. It is preferred that the glass ceramic or the glass is shaped into the desired dental restoration by pressing or machining.

The pressing is usually carried out at increased pressure and increased temperature. It is preferred that the pressing is carried out at a temperature of from 700 to 1200° C. It is further preferred to carry out the pressing at a pressure of from 2 to 10 bar. During pressing, the desired shape change is achieved by viscous flow of the material used. The starting glass according to the invention and in particular the glass with nuclei according to the invention, the lithium metasilicate glass ceramic according to the invention and the lithium disilicate glass ceramic according to the invention can be used for the pressing. The glasses and glass ceramics according to the invention can be used in particular in the form of blanks, e.g. solid blanks or powder green compacts, e.g. in unsintered, partly sintered or densely-sintered form.

The machining is usually carried out by material removing processes and in particular by milling and/or grinding. It is particularly preferred that the machining is carried out as part of a CAD/CAM process. The starting glass according to the invention, the glass with nuclei according to the invention, the lithium metasilicate glass ceramic according to the invention and the lithium disilicate glass ceramic according to the invention can be used for the machining. The glasses and glass ceramics according to the invention can be used in particular in the form of blanks, e.g. solid blanks or powder green compacts, e.g. in unsintered, partly sintered or densely-sintered form. The lithium metasilicate glass ceramic according to the invention and the lithium disilicate glass ceramic according to the invention are preferably used for the machining. The lithium disilicate glass ceramic can also be used in a not yet fully crystallized form which was produced by heat treatment at a lower temperature. This has the advantage that an easier machining, and thus the use of simpler equipment for the machining, is possible. After the machining of such a partly crystallized material, the latter is usually subjected to a heat treatment at a higher temperature and in particular about 520 to 750° C. in order to effect further crystallization of lithium disilicate.

In general, after the preparation of the dental restoration shaped as desired by pressing or machining, the latter can also in particular be heat-treated in order to convert the precursors used, such as starting glass, glass with nuclei or lithium metasilicate glass ceramic, into lithium disilicate glass ceramic or to increase the crystallization of lithium disilicate or to reduce the porosity, e.g. of a porous powder green compact used.

However, the glass ceramic according to the invention and the glass according to the invention are also suitable as coating material of e.g. ceramics and glass ceramics. The invention is therefore also directed to the use of the glass according to the invention or the glass ceramic according to the invention for coating of in particular ceramics and glass ceramics.

The invention also relates to a process for coating ceramics and glass ceramics, wherein the glass ceramic according to the invention or the glass according to the invention is applied to the ceramic or glass ceramic and is subjected to increased temperature.

This can take place in particular by sintering-on and preferably by pressing-on. With sintering-on, the glass ceramic or the glass is applied to the material to be coated, such as ceramic or glass ceramic, in the usual way, e.g. as powder, and then sintered at increased temperature. With the preferred pressing-on, the glass ceramic according to the invention or the glass according to the invention is pressed on, e.g. in the form of powder green compacts or monolithic blanks, at an increased temperature of e.g. from 700 to 1200° C., applying pressure, e.g. 2 to 10 bar. The methods described in EP 231 773 and the press furnace disclosed there can be used in particular for this. A suitable furnace is e.g. the Programat EP 5000 from Ivoclar Vivadent AG, Liechtenstein.

It is preferred that, after conclusion of the coating process, the glass ceramic according to the invention is present with lithium disilicate as main crystal phase, as it has particularly good properties.

Because of the above-described properties of the glass ceramic according to the invention and the glass according to the invention as its precursor, these are suitable in particular for use in dentistry. A subject of the invention is therefore also the use of the glass ceramic according to the invention or the glass according to the invention as a dental material and in particular for the preparation of dental restorations or as a coating material for dental restorations, such as crowns, bridges and abutments.

Finally, the glasses and glass ceramics according to the invention can also be mixed together with other glasses and glass ceramics in order to produce dental materials with properties adjusted as desired. Compositions and in particular dental materials which comprise the glass according to the invention or the glass ceramic according to the invention in combination with at least one other glass and/or one other glass ceramic therefore represent a further subject of the invention. The glass according to the invention or the glass ceramic according to the invention can therefore be used in particular as main component of an inorganic-inorganic composite or in combination with a plurality of other glasses and/or glass ceramics, wherein the composites or combinations can be used in particular as dental materials. The combinations or composites can particularly preferably be present in the form of sintered blanks. Examples of other glasses and glass ceramics for the preparation of inorganic-inorganic composites and of combinations are disclosed in DE 43 14 817, DE 44 23 793, DE 44 23 794, DE 44 28 839, DE 196 47 739, DE 197 25 553, DE 197 25 555, DE 100 31 431 and DE 10 2007 011 337. These glasses and glass ceramics belong to the group of silicates, borates, phosphates or aluminosilicates. Preferred glasses and glass ceramics are of $SiO_2$—$Al_2O_3$—$K_2O$ type (with cubic or tetragonal leucite crystals), $SiO_2$—$B_2O_3$—$Na_2O$ type, alkali-silicate type, alkali-zinc-silicate type, silicophosphate type, $SiO_2$—$ZrO_2$ type and/or lithium-aluminosilicate type (with spodumene crystals). By mixing such glasses or glass ceramics with the glasses and/or glass ceramics according to the invention, for example the coefficient of thermal expansion can be adjusted as desired in a broad range of from 6 to $20 \cdot 10^{-6}$ $K^{-1}$.

The invention is explained in more detail below by means of examples.

EXAMPLES

Examples 1 to 7—Composition and Crystal Phases

A total of 7 glasses and glass ceramics according to the invention with the composition given in Table I were prepared by melting corresponding starting glasses followed by heat treatment for controlled nucleation and crystallization.

For this, the starting glasses weighing from 100 to 200 g were first melted from usual raw materials at 1400 to 1500° C., wherein the melting was very easily possible without formation of bubbles or streaks. By pouring the starting glasses into water, glass frits were prepared which were then melted a second time at 1450 to 1550° C. for 1 to 3 h for homogenization.

In the case of Examples 1 to 6, the obtained glass melts were then poured into preheated moulds in order to produce glass monoliths.

In the case of Example 7, the obtained glass melt was cooled to 1400° C. and converted to a fine-particle granular material by pouring into water. The granular material was dried and ground to a powder with a particle size of <90 µm. This powder was moistened with some water and pressed to form a powder green compact at a pressing pressure of 20 MPa.

The glass monoliths (Examples 1-6) as well as the powder green compact (Example 7) were then converted by thermal treatment to glasses and glass ceramics according to the invention. The thermal treatments used for controlled nucleation and controlled crystallization are also given in Table I. The following meanings apply $T_N$ and $t_N$ temperature and time used for nucleation
$T_C$ and $t_C$ temperature and time used for crystallization of lithium disilicate
LP lithium orthophosphate It can be seen that a first heat treatment in the range of from 480 to 500° C. resulted in the formation of lithium silicate glasses with nuclei and these glasses already crystallized due to a further heat treatment at 520 to 750° C. within only 20 to 30 min to glass ceramics with lithium disilicate as main crystal phase, as was established by X-ray diffraction tests.

The produced lithium disilicate glass ceramics were able to be very satisfactorily machined into the form of various dental restorations, in a CAD/CAM process or by hot pressing, which restorations were also provided with a veneer if required.

They were also able to be applied by hot pressing as coatings onto in particular dental restorations, e.g. in order to veneer the latter as desired.

Example 8—Processing Via Powder Green Compacts

The glass ceramics according to Examples 1, 3, 4, 5 and 6 were ground to powders with an average particle size of <90 µm.

In a first variant, the obtained powders were pressed with or without pressing auxiliaries to powder green compacts and the latter were partly or densely sintered at temperatures of from 800 to 1100° C. and then further processed by machining or by hot pressing to form dental restorations.

In a second variant, the obtained powders were pressed with or without pressing auxiliaries to powder green compacts and the latter were then further processed by machining or by hot pressing to form dental restorations. In particular, the dental restorations obtained after the machining were then densely sintered at temperatures of from 900 to 1100° C.

With both variants, in particular crowns, caps, partial crowns and inlays as well as coatings on dental ceramics and dental glass ceramics were prepared.

Example 9—Hot Pressing of Glass with Nuclei

A glass with the composition according to Example 7 was prepared by mixing corresponding raw materials in the form of oxides and carbonates for 30 min in a Turbula mixer and then melting the mixture at 1450° C. for 120 min in a platinum crucible. The melt was poured into water in order to obtain a fine-particle granular glass material. This granular glass material was melted again at 1530° C. for 150 min in order to obtain a glass melt with particularly high homogeneity. The temperature was reduced to 1500° C. for 30 min and cylindrical glass blanks with a diameter of 12.5 mm were then poured into pre-heated, separable steel moulds or graphite moulds. The obtained glass cylinders were then nucleated at 490° C. and stress-relieved.

The nucleated glass cylinders were then processed by hot pressing at a pressing temperature of 970° C. and a pressing time of 6 min using an EP600 press furnace, Ivoclar Vivadent AG, to form dental restorations, such as inlays, onlays, veneers, partial crowns, crowns, laminating materials and laminates. In each case, lithium disilicate was detected as main crystal phase.

The invention claimed is:

1. Lithium silicate glass ceramic for the preparation of dental restorations for use in the oral cavity from said glass ceramic or for the coating of dental restorations for use in the oral cavity with said glass ceramic, wherein said glass ceramic comprises a hexavalent metal oxide selected from $MoO_3$, $WO_3$ and mixtures thereof and 12.0 to 20.0 wt.-% $Li_2O$ and comprises less than 0.5 wt.-% $K_2O$.

2. Glass ceramic according to claim 1, which comprises less than 0.1 wt.-% $K_2O$.

3. Glass ceramic according to claim 1, which comprises less than 1.0 further alkali metal oxide.

4. Glass ceramic according to claim 1, which comprises the hexavalent metal oxide or mixtures thereof in an amount of from 0.1 to 8.4 wt.-%.

5. Glass ceramic according to claim 1, which has lithium metasilicate as main crystal phase.

6. Glass ceramic according to claim 1, which has lithium disilicate as main crystal phase.

7. Glass ceramic according to claim 1, which comprises 60.0 to 85.0 wt.-% $SiO_2$.

8. Glass ceramic according to claim 1, which comprises 15.0 to 17.0 wt.-% $Li_2O$.

9. Glass ceramic according to claim 1, which comprises 0 to 10.0 wt.-% $P_2O_5$.

10. Glass ceramic according to claim 1, wherein lithium silicate glass ceramic is excluded which comprises at least 6.1 wt.-% $ZrO_2$.

11. Glass ceramic according to claim 1, wherein lithium silicate glass ceramic is excluded which comprises at least 8.5 wt.-% transition metal oxide selected from the group consisting of oxides of yttrium, oxides of transition metals with an atomic number from 41 to 79 and mixtures of these oxides.

12. Glass ceramic according to claim 1, which comprises at least one of the following components:

TABLE I

| Composition | Example 1 wt.-% | 2 wt.-% | 3 wt.-% | 4 wt.-% | 5 wt.-% | 6 wt.-% | 7 wt.-% |
| --- | --- | --- | --- | --- | --- | --- | --- |
| $SiO_2$ | 73.8 | 73.8 | 69.4 | 73.8 | 76.4 | 73.8 | 76.3 |
| $Li_2O$ | 15.3 | 15.3 | 19.7 | 15.3 | 12.7 | 15.3 | 15.9 |
| $P_2O_5$ | 3.4 | 3.4 | 3.4 | 3.4 | 3.4 | 7.0 | — |
| $Al_2O_3$ | 3.5 | — | 3.5 | 3.5 | 3.5 | — | 3.6 |
| $ZrO_2$ | — | 3.5 | — | — | — | — | — |
| $MoO_3$ | 4.0 | — | 4.0 | 2.0 | 4.0 | — | 2.1 |
| $WO_3$ | — | 4.0 | — | 2.0 | — | 3.9 | 2.1 |
| $SiO_2/Li_2O$ molar ratio | 2.39 | 2.39 | 1.75 | 2.39 | 3.00 | 2.39 | 2.39 |
| Optical properties (after pouring) | transparent | transparent | transparent | transparent | opaque glass | opaque glass | transparent |
| $T_g/°$ C. | 471 | 466 | 456 | 470 | 479 | 460 | 471 |
| $T_N/°$ C. | 490 | 490 | 480 | 490 | 500 | 480 | 490 |
| $t_N$/min. | 10 | 10 | 10 | 10 | 10 | 10 | 10 |
| $T_c/°$ C. | 520 | 700 | 650 | 740 | 750 | 750 | 750 |
| $t_c$/min. | 20 | 20 | 20 | 30 | 30 | 20 | 30 |
| Main crystal phase RT-XRD | lithium disilicate | lithium disilicate | lithium disilicate | lithium disilicate | lithium disilicate | lithium disilicate | lithium disilicate |
| Other phases | $Li_3PO_4$, | — | LP, quartz | — | LP | LP | — |

| Component | wt.-% |
| --- | --- |
| SiO$_2$ | 69.0 to 77.0 |
| hexavalent metal oxide or mixtures | 2.0 to 5.0 |
| P$_2$O$_5$ | 0 to 7.0 |
| Al$_2$O$_3$ | 0 to 6.0. |

13. Lithium silicate glass ceramic according to claim 1, which has lithium disilicate as main crystal phase and a fracture toughness, measured as $K_{IC}$ value, of at least 1.5 MPa·10$^{-5}$.

14. Lithium silicate glass ceramic according to claim 1, which comprises SiO$_2$ and Li$_2$O in a molar ratio of from 1.7 to 3.1.

15. Glass ceramic according to claim 1, wherein the glass ceramic is present in the form of a powder, a granular material, a blank or a dental restoration.

16. Process for the preparation of the glass ceramic according to claim 1, wherein a starting glass, a glass with nuclei or a glass ceramic with lithium metasilicate as main crystal phase is subjected to at least one heat treatment in the range of from 450 to 950° C.

17. Process for the preparation of a lithium silicate glass ceramic which comprises a hexavalent metal oxide selected from MoO$_3$, WO$_3$ and mixtures thereof, wherein
(a) a starting glass which comprises the components of the glass ceramic is subjected to a heat treatment at a temperature of from 480 to 500° C. in order to form a glass with nuclei which are suitable for forming lithium disilicate crystals, and
(b) the glass with nuclei is subjected to a heat treatment at a temperature of from 520 to 750° C. in order to form a glass ceramic with lithium disilicate as main crystal phase.

18. Process of using a lithium silicate glass ceramic, or a glass with nuclei which are suitable for forming lithium metasilicate and/or lithium disilicate crystals, wherein the glass ceramic and the glass comprise a hexavalent metal oxide selected from MoO$_3$, WO$_3$ and mixtures thereof, as a dental material comprising preparing a dental restoration for use in the oral cavity from said glass ceramic or coating a dental restoration for use in the oral cavity with said glass ceramic.

19. Process according to claim 18, wherein preparing or coating the dental restoration comprises shaping by pressing or machining the glass ceramic or the glass to the dental restoration.

20. Lithium silicate glass ceramic which comprises a hexavalent metal oxide selected from MoO$_3$, WO$_3$ and mixtures thereof and 15.0 to 20.0 wt.-% Li$_2$O.

21. Lithium silicate glass with nuclei which are suitable for forming lithium metasilicate and/or lithium disilicate crystals, wherein the glass comprises a hexavalent metal oxide selected from MoO$_3$, WO$_3$ and mixtures thereof and 15.0 to 20.0 wt.-% Li$_2$O.

* * * * *